United States Patent
Moe et al.

(10) Patent No.: US 6,283,995 B1
(45) Date of Patent: *Sep. 4, 2001

(54) HEART VALVE LEAFLET WITH SCALLOPED FREE MARGIN

(75) Inventors: Riyad E. Moe; Edward J. Sarnowski, both of Austin, TX (US)

(73) Assignee: Sulzer Carbomedics Inc., Austin, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/292,485

(22) Filed: Apr. 15, 1999

(51) Int. Cl.[7] .......................................................... A61F 2/24
(52) U.S. Cl. .......................................... 623/2.19; 623/2.12
(58) Field of Search ...................................... 623/2.1, 2.12, 623/2.14, 2.15, 2.3, 2.19, 2.13

(56) References Cited

U.S. PATENT DOCUMENTS

| | | | |
|---|---|---|---|
| 4,291,420 | * 9/1981 | Reul | 623/2.1 |
| 4,364,127 | * 12/1982 | Pierce et al. | 623/2.1 |
| 4,473,423 | 9/1984 | Kolff | 156/245 |
| 4,778,461 | 10/1988 | Pietsch et al. | 623/2 |
| 4,888,009 | 12/1989 | Lederman et al. | 623/2 |
| 5,116,564 | 5/1992 | Jansen et al. | 264/255 |
| 5,500,016 | 3/1996 | Fisher | 623/2 |
| 5,562,729 | 10/1996 | Purdy et al. | 623/2 |
| 5,713,953 | * 2/1998 | Vallana et al. | 623/2.11 |
| 6,117,169 | * 9/2000 | Moe | 623/2.12 |

FOREIGN PATENT DOCUMENTS

97/41808 * 11/1997 (WO) .................................... 623/2.1

WO 98/32400    7/1998 (WO) .

OTHER PUBLICATIONS

In Vitro & Durability Assessment of Novel Polyurethane Heart Valve, Mackay et al, Artifircal Organs, vol. 20, Sep. 1996.*

Polyurethane Artifical Heart Valves in Animals Akutsu et al, pp. 1045–1048.*

New J–3 Flexible–Leaflet Polyurethane Heart Valve Jansen et al, Artifical Organs vol. 14, Oct. 1991.*

Mohamed S. Hamid et al., "Influence of Stent Height Upon Stresses on the Susps of Closed Bioprosthetic Valves", 1986, vol. 19, No. 9, pp. 759–769.

J. Fisher et al., "An Improved Pericardial Biprosthetic Heart Valve", 1987, 1: 71–79.

Grant W. Christie, On Stress Reduction in Bioprosthetic Heart Valve Leaflets by the Use of a Flexible Stent, 1991, vol. 6, No. 4, pp 476–181.

G. W. Christie, "The Bovine Pericardial Bioprosthetic Heart Valve: Methods for Tensile Stress Reduction in the Leaflets During the Loaded Phase", 1991, vol. 20, pp. 647–650.

* cited by examiner

Primary Examiner—Bruce Snow
(74) Attorney, Agent, or Firm—Blossom E. Loo

(57) ABSTRACT

A heart valve prosthesis includes a molded body and a plurality of leaflets. Each leaflet includes a free margin having opposite ends and a mid-point. The opposite ends are attached to a peripheral portion of the valve. Each free margin is adjacent each other free margin to form a natural-state non-uniform gap therebetween. The gap has a maximized width adjacent the mid-point of each leaflet. Each free margin is scalloped to form a peak at the opposite ends and a mid-point peak between the opposite ends. Each peak is substantially the same height above the base.

24 Claims, 2 Drawing Sheets

HEART VALVE LEAFLET WITH SCALLOPED FREE MARGIN

BACKGROUND

The disclosures herein relate generally to heart valves and more particularly to tri-leaflet polymer valves.

Heart valves include mechanical valves, tissue valves and polymer valves. A heart valve is implanted into an annular opening in a heart created when a diseased valve is removed. The valve can be secured in the annulus of the opening through the use of sutures or pins that penetrate the host tissue and an outside edge of the valve. Alternatively, the valve can then be secured in the annulus by suturing the host tissue to the sewing ring. Heart valves function essentially as a one-way check valve.

Early heart valve prostheses included ball-and-cage valves and disc-and-cage valves in which a ball or a disc was housed in a cage. One side of the cage provided an orifice through which blood flowed either into or out of the heart, depending on the valve being replaced. When blood flowed in a forward direction, the energy of the blood flow forced the ball or disc to the back of the cage allowing blood to flow through the valve. When blood attempted to flow in a reverse direction, or "regurgitate", the energy of the blood flow forced the ball or disc into the orifice in the valve and blocked the flow of blood.

A bi-leaflet valve comprised an annular valve body in which two opposed leaflet occluders were pivotally mounted. The occluders were typically substantially rigid, although some designs incorporated flexible leaflets, and moved between a closed position, in which the two leaflets were mated and blocked blood flow in the reverse direction, and an open position, in which the occluders were pivoted away from each other and did not block blood flow in the forward direction. The energy of blood flow caused the occluders to move between their open and closed positions.

A tri-leaflet valve comprised an annular valve body in which three flexible leaflets were mounted to a portion of the valve body, called a "stent," located at the circumference of the annulus. Some tri-leaflet valves used rigid leaflets. When blood flowed in the forward direction, the energy of the blood flow deflected the three leaflets away from the center of the annulus and allowed blood to flow through. When blood flowed in the reverse direction, the three leaflets engaged each other in a coaptive region, occluded the valve body annulus and prevented the flow of blood. The valve leaflets were made from tissue, such as specially treated porcine or bovine pericardial tissue or from a man-made material such as polyurethane or another biocompatible polymer.

In one specific example, i.e. U.S. Pat. No. 4,364,127, a prosthetic heart valve constructed of hemo-compatible materials that is anatomically and functionally similar to the natural aortic valve is disclosed. The heart valve is a tri-leaflet type which has its formed leaflets heat set in a partially open position to reduce pressure required to open the leaflets in response to blood flowing therethrough.

U.S. Pat. No. 4,473,423 discloses an artificial heart valve having thin, seamless leaflets which converge to the center of a frame from the frame's inner wall. The leaflets each have a convex outflow surface and a concave inflow surface. The leaflets meet along adjacent edges to form cusps. Sinus valsalvae sections of the valve are formed as rounded recesses defined in the valve frame's inner wall as continuous curved profiles of the respective leaflet concave surface. The valve is fabricated by vacuum molding techniques whereby layers of elastomer are vacuum formed to comprise the leaflet and sinus valsalvae portions. The leaflets are all formed from two or more layers of elastomer which are cut to define the leaflet edges or commissures. One elastomer layer extends along the frame recess to provide continuity for each leaflet and its sinus valsalvae. The resulting structure has no rims or seams in the inflow or outflow paths.

In U.S. Pat. No. 4,778,461, a heart valve prosthesis for replacing the aortic valve or the pulmonary valve, comprises a support ring with at least two commissure supports and flexible cusps, is characterized in that the height of the support ring including the commissure supports is less than the total height of the heart valve prosthesis.

In U.S. Pat. No. 4,888,009, a prosthetic heart valve comprises a suture ring supporting a stent which surrounds a conduit bearing a plurality of flexible valve leaflets. The conduit extends beyond the end of the suture ring.

U.S. Pat. No. 5,116,564 discloses a method of producing flexible closing members, especially artificial heart valves. The housing of the closing member is radially expanded, the closing element of the closing member is formed as a substantially plane two-dimensional element, and the plane two-dimensional element is connected to the housing in the expanded condition of the same. This method is preferably realized as a dip method according to which the closing element is shaped and formed to the housing in a single working step. The described flexible closing member is an artificial three-sail heart valve which is characterized by a special shape of the three closing elements.

In U.S. Pat. No. 5,500,016, a flexible leaflet heart valve, to replace natural aortic or pulmonary valves of the heart, includes a frame and flexible leaflets attached to the frame. Each flexible leaflet forms part of a surface of revolution having its axis of revolution substantially orthogonal to the direction of blood flow through the valve.

U.S. Pat. No. 5,562,729 discloses a multi-leaflet heart valve composed of a biocompatible polymer which, simultaneously imitates the structure and dynamics of biological heart valves and avoids promotion of calcification. The valve includes a plurality of flexible leaflets dip cast on a mandrel, which leaflets are then bonded with a bonding agent to the interior surfaces of a plurality of struts on a metal-reinforced prosthetic stent. The leaflets open and close in response to the pumping action of the heart. The leaflets and the polymer components of the prosthetic stent are manufactured of biocompatible polymers exhibiting intrinsic calcification-resistant properties.

An important consideration in prosthetic heart valve design is the durability of the heart valve. Replacing a prosthetic heart valve after it has been implanted is inconvenient and expensive for the patient. Mechanical valves may enhance the possibility of clotting. Therefore, patients using mechanical valves are typically required to take anticoagulation medication. Also, mechanical valves are noisy which is most disconcerting to patients. Patients having tissue valve implants are usually not required to take anticoagulation medication. Tissue valves are not noisy like mechanical valves however, they are also not very durable.

Polymer valves are typically molded to a desired shape and then cut to form the free margins of the leaflets. One source of prosthetic heart valve failure is tearing. Cutting to form the free margins of the leaflets may introduce imperfections in the polymer which can lead to eventual failure of the valve. Therefore, cutting creates durability problems at the cut surfaces.

A factor in heart valve design is the consideration of energy loss. It is important to design a heart valve in a manner that will provide low energy loss. Energy loss considerations include forward pressure drop, leakage volume and closing volume. A major limitation of many known polymer valves is that, due to their geometry, they have significant planar coaption surfaces in the at rest or natural-state condition to provide good closure characteristics, but this causes the heart to work harder to open the valve. Other known polymer valves include geometries that are easier to open but the neutral position gap area is exaggerated. This increases closing volume which increases energy loss.

Therefore what is needed is a molded heart valve, preferably of polymer or other suitable material, which is durable, does not require cutting, provides low energy loss, and does not require the heart to work harder in cooperation with the functioning of the valve.

SUMMARY

One embodiment, accordingly, provides a heart valve which includes a scallop in the free margin at the adjacent midpoints of the leaflets to allow for a reduced leaflet gap area. In addition, the scallop provides sufficient material at the gap center for coaption. To this end, a heart valve includes a molded body including a plurality of leaflets, each leaflet including a free margin having opposite ends and a mid-point. The opposite ends are attached to a commissure of the valve. Each free margin converges toward each other free margin to form a natural-state, non-uniform gap therebetween. Each free margin is scalloped to form a peak at the opposite ends and at a mid-point between the opposite ends.

A principal advantage of this embodiment is that a molded leaflet valve has improved structural integrity provided at lower manufacturing cost and with less complexity. The molded leaflet edge predictably has longer fatigue life than a cut leaflet edge. To reduce opening pressures, it is advantageous to provide leaflets with continuous curvature. The scallop provided in a continuous leaflet allows the mid-point and commissures to move closer together without decreasing the gap distance at the narrowest point. The scallop also results in less gap area and smaller gap distances at the commissure and the mid-point. Advantages resulting from these structural features include less regurgitation, smaller closing volume, more coaptive material at the mid-point and the commissures, and higher prolapse resistance.

BRIEF DESCRIPTION OF THE DRAWING FIGURES

DETAILED DESCRIPTION

Figure 1:
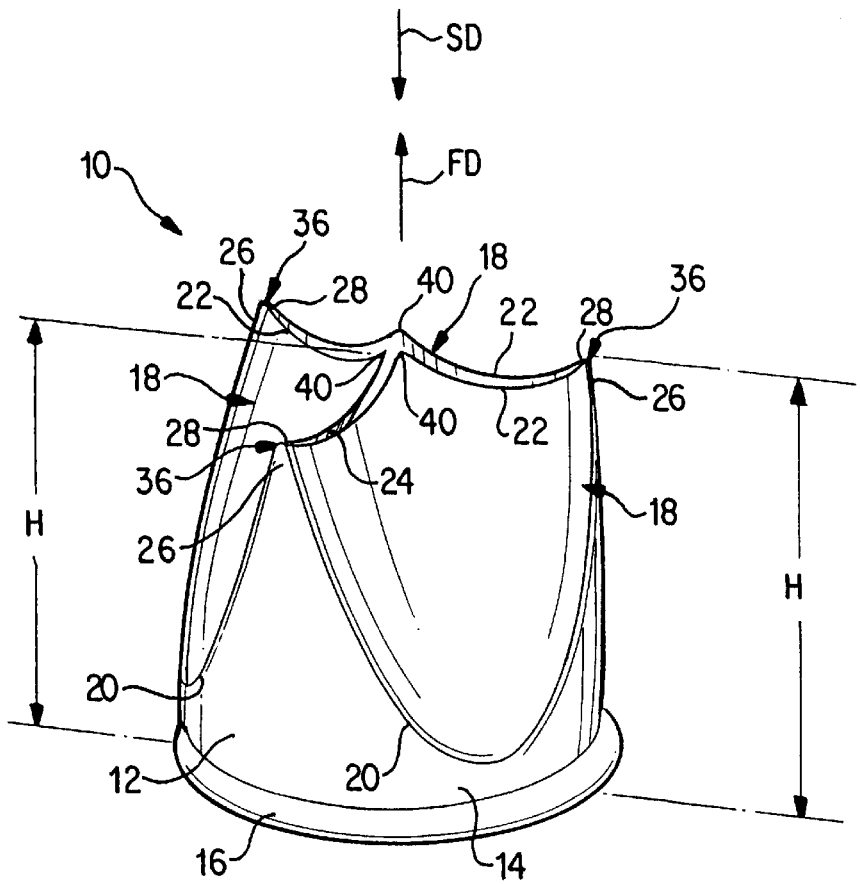
FIG. 1 is an isometric view illustrating an embodiment of a heart valve having leaflets in a natural state.

A heart valve is generally designated 10 in FIG. 1. Heart valve 10 is formed as a one-piece molded biocompatible polymer body such as silicone or polyurethane and includes a generally annular peripheral body portion 12 which has a base 14. A sewing ring 16 may be formed with the base 14. Three flexible leaflets 18 are formed with body 12 and extend from an attachment curve 20 to terminate at a free margin 22 which is not in contact with another portion of body 12 when the valve is in a natural-state condition, i.e. the valve parts are at rest and are not under the influence of any pressure acting thereon. This is in contrast with the valve after installation when the pumping action of the heart sequentially and repeatedly opens and closes the valve by urging the leaflets in a first or opening direction indicated by the arrow designated FD, and then in a second or closing direction, opposite the first direction, indicated by the arrow designated SD.

The entire heart valve 10 is molded including a gap 24 which is preferably formed between each free margin 22. This is preferred over cutting to separate the valve leaflets after molding to form the free margins and improves the durability of the valve 10.

The attachment curve 20 defines a coupling between each leaflet 18 and the peripheral body portion 12, and also defines three shaped posts 26 which comprise an extension of body 12 terminating at a commissure 28 where gap 24 ends. This corresponds to the location where each leaflet 18 comes together with an adjacent leaflet. Posts 26 and each commissure 28 are at a height H above base 14.

Figure 2:
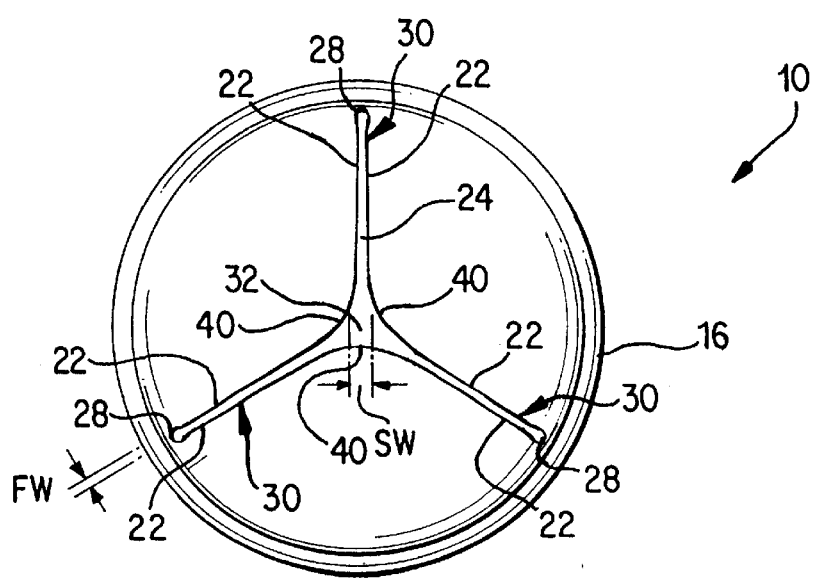
FIG. 2 is a top view illustrating an embodiment of the heart valve having leaflets in the natural state.

Each free margin 22, FIG. 2, terminates adjacent each other free margin 22 to form the natural-state non-uniform gap 24. Gap 24 includes three legs 30 in the tri-leaflet configuration illustrated. Each leg 30 has a substantially uniform first width FW. Each leg 30 extends between its respective commissure 28 and a central opening 32 of gap 24 which interconnects each leg 30. Central opening 32 had a maximum second width SW which is greater than the first width FW.

Figure 3:
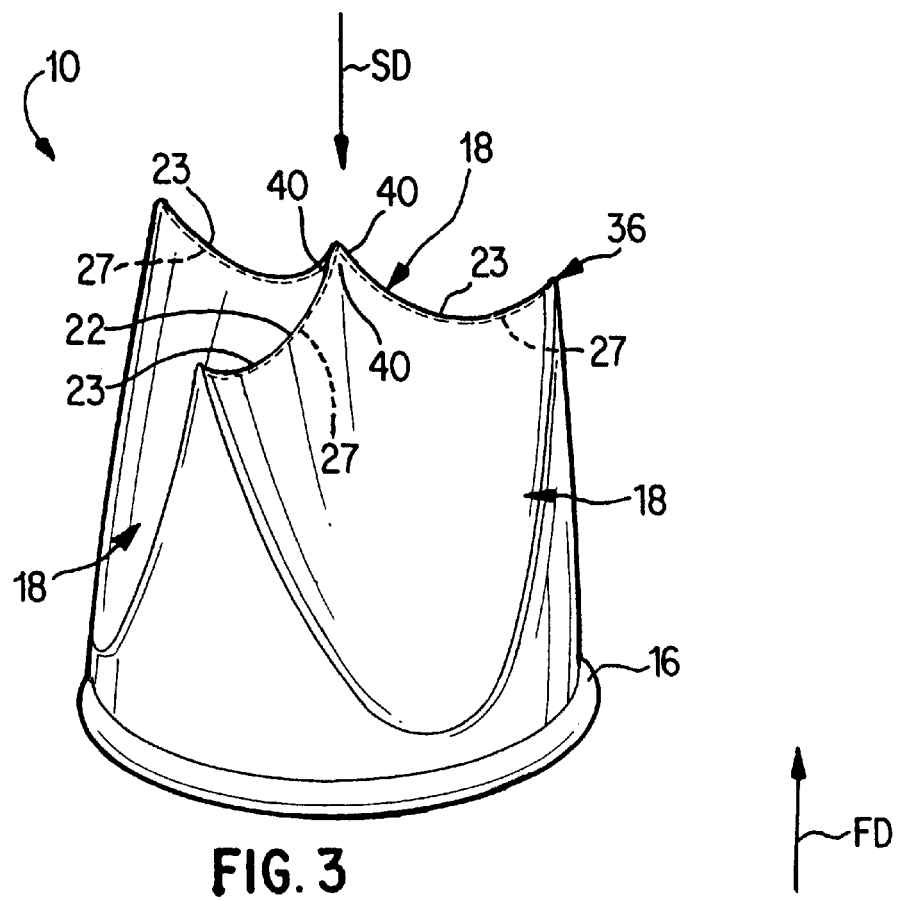
FIG. 3 is an isometric view illustrating an embodiment of the heart valve having leaflets in a closed position.

In order for gap 24 to be fully closed during operation of valve 10, FIGS. 1 and 2, each free margin 22 is scalloped to form a peak 36 at the opposite ends adjacent the respective commissures 28, and a mid-point peak 40 between the commissures 28 and adjacent the central opening 32. Each peak 36 and 40 is of the height H above base 14 which is substantially the same height H as posts 26 and commissures 28. Each mid-point peak 40, FIG. 3, is also of sufficient height to converge with each other mid-point peak 40 to a substantially closed position in response to reverse blood flow in the direction indicated by arrow SD, in response to the pumping action of the heart. Scallops 23 formed in the free margin 22 between each peak 36 at the opposite ends, and the mid-point peak 40, allow for a reduced leaflet gap 24 adjacent the legs 30, and also increase the overall length of the free margin 22. The peaks 40 cooperate upon closure of valve 10 to allow for sufficient material at the central opening 32 for coaption as indicated by the dotted lines 27 adjacent the scallops 23. If desired, the geometry of scallops 23, peaks 36 and 40 can be altered to tailor the profile of gap 24.

Figure 4:
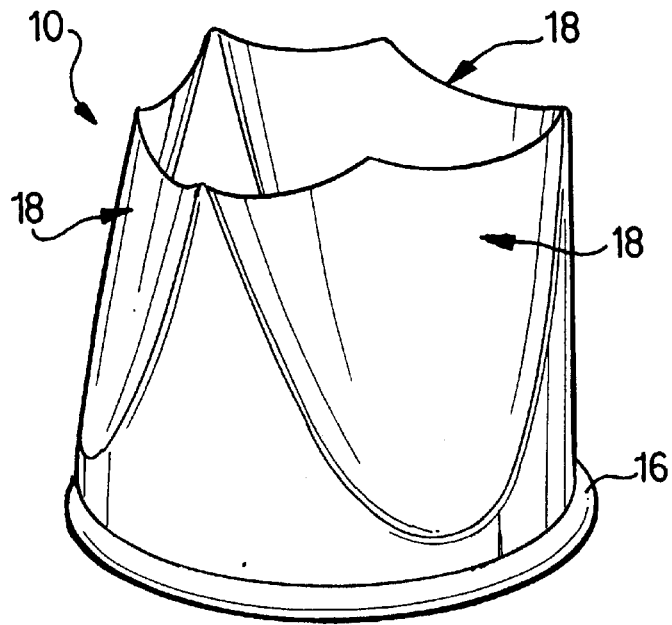
FIG. 4 is an isometric view illustrating an embodiment of the heart valve having leaflets in an open position.

In operation, when fluid flow is in the forward direction as indicated by arrow FD, FIG. 4, the pressure of the blood flow causes leaflets 18 to deflect to the open position. In this open position, the leaflets 18 define a large flow orifice such that the leaflets 18 present little resistance to fluid flow.

When fluid flow is in the reverse direction as indicated by arrow SD, FIG. 3, the pressure of the blood flow causes leaflets 18 to deflect to the closed position. In this closed position, the leaflets 18 occlude at the free margins 22 so that gap 24 is closed. Coaption occurs but is minimized due to the natural gap 24. Thus, closure to seal against reverse flow is accomplished as is improved occlusion and coaption.

As a result, one embodiment provides a heart valve 10 including a molded body having a plurality of leaflets 18. Each leaflet 18 has a free margin 22 including opposite ends and a mid-point. The opposite ends are attached to a peripheral portion 12 of the valve. Each free margin 22 is adjacent each other free margin 22 to form a neutral-state non-uniform gap 24 therebetween. Each free margin 22 is scalloped to form a peak 36 at the opposite ends and at a mid-point peak 40 between the opposite ends.

Another embodiment provides a heart valve prosthesis 10 including a molded body having a base 14 and a plurality of leaflets 18. Each leaflet 18 includes a free margin 22 having opposite ends and a mid-point. The opposite ends are attached to a peripheral portion 22 of the valve. Each free margin 22 is adjacent each other free margin 22 to form a natural-state non-uniform gap 24 therebetween. The gap 24 is maximized adjacent the mid-point 40 of each leaflet. Each free margin 22 is scalloped to form a peak 36 at the opposite ends and a mid-point peak 40 between the opposite ends. Each peak 36, 40 is substantially the same height H above the base 14.

Still another embodiment provides a method of forming a flexible heart valve 10 including molding a one-piece body 12 having a base 14 and a plurality of flexible relatively movable leaflets 18. Each leaflet 18 is formed to include a free margin 22 having opposite ends and a mid-point between the opposite ends. The opposite ends are extended to integrally connect to a peripheral portion 12 of the valve. Each molded free margin 22 is shaped to terminate adjacent each other free margin to define a continuous natural-state non-uniform gap 24 therebetween which is maximized adjacent the mid-point of each leaflet. Also, each molded free margin 22 is shaped to include scallops forming a peak 36 at the opposite ends and a peak 40 at the mid-point so that each peak 36, 40 extends to a substantially equal height H above the base 14.

A further embodiment provides a flexible leaflet heart valve 10 including a molded body 12 and at least three leaflets 18. Each leaflet 18 includes a free margin 22 having opposite ends and a mid-point. The opposite ends are attached to a peripheral portion 12 of the valve. Each free margin is adjacent each other free margin to form a natural-state non-uniform gap 24 therebetween. The gap 24 includes at least three legs 30 having a substantially uniform first width FW, and a central opening 32 having a second width SW greater than the first width FW. The central opening 32 interconnects the three legs 30. Each free margin 22 is scalloped to form a peak 36 at the opposite ends and a mid-point peak 40 adjacent the central opening 32.

Although illustrative embodiments have been shown and described, a wide range of modification change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A heart valve prosthesis comprising:
   a peripheral valve body;
   at least three polymeric leaflets, each leaflet comprising a free margin having opposite ends attached to said peripheral valve body and a mid-point, each said free margin being adjacent another free margin to form a plurality of adjacent free margin pairs, and each free margin being scalloped to form a peak at each of said opposite ends and a mid-point peak between said opposite ends; and
   a plurality of natural state non-uniform gaps formed between each of said adjacent free margin pairs, said gaps having a first width adjacent said opposite ends and a second width adjacent said mid-point, said second width being greater than said first width.

2. The heart valve of claim 1 wherein the peripheral valve body comprises an annular surface.

3. The heart valve of claim 2 wherein the annular surface comprises a plurality of commissures formed therewith.

4. The heart valve as defined in claim 3 wherein the opposite ends terminate adjacent a respective one of the commissures.

5. The heart valve of claim 1 wherein the body includes a base having a sewing ring formed therewith.

6. The heart valve of claim 1 wherein the body includes a base, each peak extending to a substantially equal height above the base.

7. The heart valve of claim 1 wherein the leaflets are molded.

8. The heart valve of claim 1 further comprising a central opening the mid-point peak being adjacent the central opening.

9. The heart valve of claim 1 wherein each mid-point peak is of a height sufficient to contact each other mid-point peak in response to each free margin being urged toward each other free margin.

10. A heart valve prosthesis comprising:
    a valve body comprising a base and a plurality of polymeric leaflets, each leaflet comprising a free margin having opposite ends attached to said valve body and a mid-point;
    each free margin being adjacent another free margin to form a natural-state nonuniform gap therebetween, the gap having a maximized width adjacent the mid-point of each leaflet; and
    each free margin being scalloped to form a peak at each of the opposite ends and a mid-point peak between the opposite ends, each peak being of substantially equal height above the base.

11. The heart valve of claim 10 wherein the valve body further comprises a peripheral portion comprising an annular surface.

12. The heart valve as defined in claim 11 wherein the annular peripheral surface includes a plurality of commissures formed therewith.

13. The heart valve as defined in claim 12 wherein the opposite ends terminate adjacent a respective one of the commissures.

14. The heart valve of claim 10 wherein the body includes a base having a sewing ring formed therewith.

15. The heart valve of claim 10 wherein the body molded.

16. The heart valve of claim 10 further comprising a central opening, the mid-point peak being adjacent the central opening.

17. The prosthetic heart valve as defined in claim 10 wherein each mid-point peak is of a height sufficient to converge with each other mid-point peak to a substantially closed position in response to each free margin being urged toward each other free margin.

18. A flexible leaflet heart valve comprising:
    a body and at least three leaflets, each leaflet including a free margin having opposite ends and a mid-point, the opposite ends being attached to a peripheral portion of the valve;
    each free margin being adjacent each other free margin to from a natural-state non-uniform gap therebetween, the gap including at least three legs having a substantially uniform first width and a central opening having a second width greater than the first width interconnecting the three legs; and
    each free margin being scalloped to form a peak at the opposite ends and a mid-point peak adjacent the central opening.

19. The heart valve of claim 18 wherein the peripheral portion of the valve comprises an annular surface comprising a plurality of commissures formed therewith.

20. The heart valve as defined in claim 19 wherein the opposite ends terminate adjacent a respective one of the commissures.

21. The heart valve of claim 18 wherein the body is molded and comprises a base having a sewing ring formed therewith.

22. The heart valve of claim 18 wherein the body comprises a base, each peak extending to a substantially equal height above the base.

23. The heart valve as defined in claim 18 wherein each leaflet free margin is molded.

24. The heart valve as defined in claim 18 wherein each leaflet free margin is molded separate from each other leaflet margin.

* * * * *